US012721528B2

(12) United States Patent
Bermak et al.

(10) Patent No.: US 12,721,528 B2
(45) Date of Patent: Sep. 1, 2026

(54) SENSORS FOR WEARABLE ELECTRONICS

(71) Applicant: Qatar Foundation for Education, Science and Community Development, Doha (QA)

(72) Inventors: Amine Bermak, Doha (QA); Saleem Khan, Doha (QA); Shawkat Ali, Doha (QA)

(73) Assignee: HAMAD BIN KHALIFA UNIVERSITY, Doha (QA)

(*) Notice: Subject to any disclaimer, the term of this patent is extended or adjusted under 35 U.S.C. 154(b) by 765 days.

(21) Appl. No.: 17/502,802

(22) Filed: Oct. 15, 2021

(65) Prior Publication Data

US 2022/0117495 A1 Apr. 21, 2022

Related U.S. Application Data

(60) Provisional application No. 63/094,091, filed on Oct. 20, 2020, provisional application No. 63/092,888, filed on Oct. 16, 2020.

(51) Int. Cl.
*A61B 5/01* (2006.01)
*A61B 5/00* (2006.01)

(52) U.S. Cl.
CPC .............. *A61B 5/01* (2013.01); *A61B 5/6803* (2013.01); *A61B 5/6804* (2013.01); *A61B 2562/0271* (2013.01); *A61B 2562/164* (2013.01)

(58) Field of Classification Search
None
See application file for complete search history.

(56) References Cited

U.S. PATENT DOCUMENTS 9,943,252 B1 4/2018 Kayyali
2011/0087084 A1* 4/2011 Jeong ................ A61B 5/14546 600/300

FOREIGN PATENT DOCUMENTS

| | | | |
|---|---|---|---|
| CN | 104814544 | A | 8/2015 |
| CN | 107405508 | A | 11/2017 |
| WO | 2015166444 | A1 | 11/2015 |
| WO | 2016200109 | A1 | 12/2016 |
| WO | 2020092701 | A2 | 5/2020 |

OTHER PUBLICATIONS

Su, Y., Ma, C., Chen, J. et al. Printable, Highly Sensitive Flexible Temperature Sensors for Human Body Temperature Monitoring: A Review. Nanoscale Res Lett 15, 200 (2020). https://doi.org/10.1186/s11671-020-03428-4 (Year: 2020).*

* cited by examiner

*Primary Examiner* — Charles A Marmor, II
(74) *Attorney, Agent, or Firm* — K&L Gates LLP

(57) ABSTRACT

The present disclosure relates to a human body temperature sensor fabricated through inkjet material printer at room temperature in two steps deposition process. The proposed sensor consists of silver based interdigital electrode and carbon black film as sensing elements, which are sensitive towards human body temperature. In various embodiments, the present disclosure has two terminals that provide change in resistance against temperature detection. The change in resistance is directly proportional to the change in temperature i.e. positive temperature coefficient (PTC). Interdigital electrodes (IDE) fingers spacing were optimized for the high sensitivity and linear resistance behavior at a temperature range is recorded. The sensor response is very linear on the human body temperature readings.

5 Claims, 15 Drawing Sheets
(10 of 15 Drawing Sheet(s) Filed in Color)

| Days | 1 | 10 | 20 | 30 | 40 | 50 |
|---|---|---|---|---|---|---|
| Resistance (Ω) @38.5°C | 44.45 4 | 445.60 | 445.62 | 445.66 | 445.60 | 445.65 |

FIG. 9

| S.N | Temp. Range | Sensitivity | Type | Res/ Rec Time | Mat. | Ref. |
|---|---|---|---|---|---|---|
| 1 | 0-100 °C | 1.07m/°C | Resistive | ------ | Ag | [24] |
| 2 | 20-60 °C | 2.2m/ °C | Resistive | ----- | Ag | [29] |
| 3 | 20-70 °C | 4 mV/°C | Resistive | ------ | CNTs | [30] |
| 4 | 22-200 °C | 3.3m/°C | Resistive | ----- | CNTs | [3] |
| 5 | 10- 120 °C | 0.008/°C | Resistive | ------ | QDs | [26] |
| 6 | 0-120°C | 80pF/°C | Capacitive | 3/3.5 | GO | [31] |
| 7 | 28-50 °C | 3.7m/°C | Resistive | 4/8.5 | Carbon | This work |

FIG. 10

SENSORS FOR WEARABLE ELECTRONICS

CROSS-REFERENCE TO RELATED APPLICATIONS

This application claims benefit under 35 U.S.C. § 119(e) from U.S. Provisional Patent Application Ser. No. 63/092,888, filed Oct. 16, 2020, and U.S. Provisional Patent Application Ser. No. 63/094,091, filed on Oct. 20, 2020, the contents of which are incorporated herein by reference in their entirety.

FIELD

The present specification relates to wearable sensors, such as temperature sensors.

BACKGROUND

Recently, printed wearable sensors for monitoring of vital biosignals, such as body temperature, respiration rate, blood pressure, glucose and electrophysiology, have attracted tremendous interest in the biomedical research community. These sensors are developed on biocompatible substrates and integrated conformably onto a target surface. In some cases, these sensors are printed as electronic "tattoos" attached directly to the human skin, or integrated within textiles. Among the various data, human body temperature measurement is given special consideration, as it can be utilized as an early indicator for variety of diseases.

For long-term in-situ monitoring, temperature sensors should be flexible and stretchable, enabling conformable integration onto the human skin. However, commercially available sensors are typically developed on planar substrates which are rigid and cannot be applied to non-planar surfaces for wearable sensing applications.

On the other hand, the lower glass transition temperature (Tg) of polymeric substrates does not allow manufacturing of these sensors through conventional clean room processes. However, the emerging printed electronics technologies enable fabrication of electronic devices, circuits and systems on a variety of substrates at ambient conditions. A number of printing technologies have been reported recently for production of flexible electronics and sensors on polymeric substrates. Two major approaches (contact- and non-contact-based) are practiced for the development of these printing systems. In a contact-printing technique, patterned inked surfaces are brought in physical contact with the target substrate. Contact-based printing technologies include gravure printing, flexographic printing, micro-contact printing, nano-imprint and screen printing.

In non-contact printing, a solution is deposited through nozzles onto the target substrate following a pre-programmed pattern. Non-contact printing techniques include, slot-die coating, aerosol, electro-hydrodynamic, and inkjet printing. Non-contact printing techniques have received greater interest for flexible electronics manufacturing due to the attractive features such as simplicity, affordability, speed, adaptability to the fabrication process, reduced material wastage, high resolution of patterns, and easy control by adjusting few printing parameters.

Inkjet printing is the prominent non-contact technique for fabrication of electronic devices on variety of substrates at ambient conditions and is very efficient in material usage. Inkjet printer can produce patterns repeatedly at resolution as high as ~50 μm and film thicknesses of up to few nanometers. For development of sensors such as temperature sensors, a variety of materials and geometries have been adopted, such as resistive temperature sensors on paper substrate, silver meander patterns on plastic substrates and graphite-polydimethylsiloxane composite etc. All of these sensors have certain limitations, for instance temperature range, sensitivity and fabrication processes etc. Among the limitations of printed temperature sensors, drift in resistance with passage of time is one of the serious issues. In wearable electronics applications, sensors need to be stable and fabricated at room temperature over a variety of unconventional substrates such as plastic, paper and cloth.

Therefore, improved systems and methods are needed.

SUMMARY

Disclosed embodiments comprise body sensors such as temperature sensors, for example for mammals such as humans.

Disclosed embodiments comprise methods of making body sensors, including temperature sensors.

Disclosed embodiments comprise methods of using body sensors, including temperature sensors.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 9 shows an exemplary resistance reading of a disclosed sensor at 38.5° C. over time.

FIG. 10 shows an exemplary performance comparison of a disclosed sensor.

DETAILED DESCRIPTION

Figure 1:
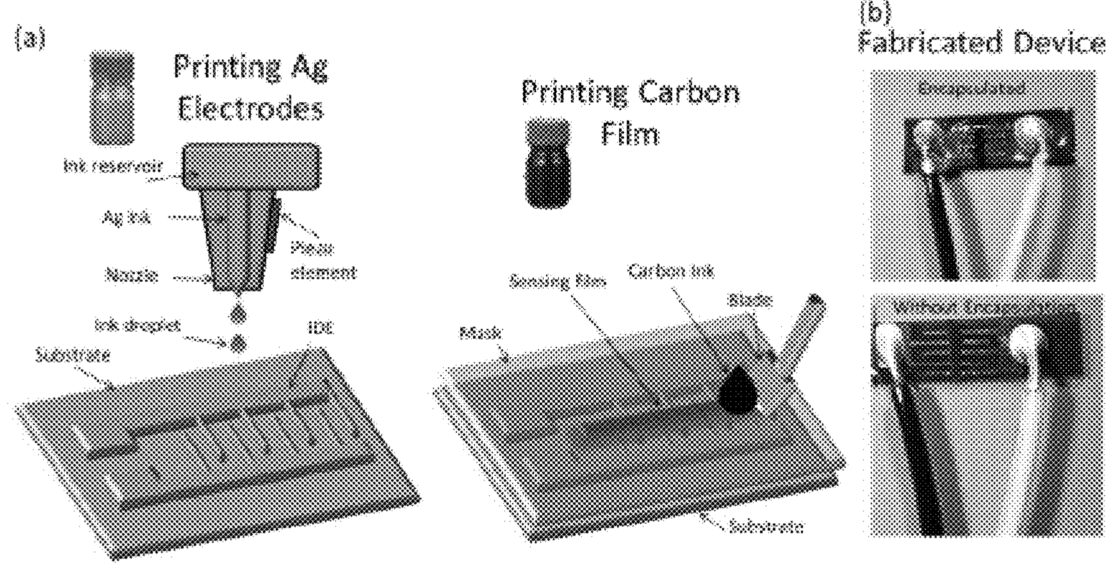
FIG. 1 shows an exemplary (a) fabrication of Ag electrodes and carbon sensing film and (b) fabricated devices bottom without encapsulation and top encapsulated with silicon epoxy.

An innovative approach towards human body temperature detection through a wearable low cost and scalable printed sensor is disclosed. An all-printing approach is introduced to directly develop sensors on a thermally sensitive substrate by using environment friendly and biocompatible materials through screen printed technology. In embodiments, an interdigital electrode structure filled with a temperature sensing layer is printed for the human body temperature detection. In embodiments, a polyimide PI substrate in combination with Polydimethylsiloxane (PDMS) encapsulation layer is utilized in the device fabrication. The thermal sensing property of the carbon black film and PI substrate is exploited to detect human body temperature.

In embodiments, mass production of the sensor at very low cost can be done with screen printing technique in 3 steps. 1) Patterning of silver IDE, 2) deposition of carbon sensing film, and 3) PDMS encapsulating layer. The proposed sensor can be scaled according to the requirement from μm to cm size.

In embodiments, a single sensor device is developed which can be placed on the human body (wrist or any temperature readable area). In embodiments, the sensor is fully encapsulated, waterproof and immune to environmental effects. In embodiments, the temperature sensor is a two terminal device that change the electrical resistance against temperature variation. Variation in resistance is transformed into voltage levels with readout circuit (a voltage divider network). In embodiments, the temperature sensor can be used in a facial mask where the sensor is interacting with inhale/exhale cycles and read the deep body temperature. In embodiments, the sensor can also be used for the respiration rate detection during inhale/exhale cycles by measuring the change in temperature. Human body temperature is very essential biomarker for early detection of various diseases. Use of human body temperature is not limited to clinics, critical patients, and infants but it can also be utilized in various applications such as sport, outdoor activity, and for construction workers etc. Deployment of this sensor on a human body will help in rapid and early detection of body temperature, and various biomarkers before going into life threatening incidents.

Sensors

Disclosed embodiments comprise body sensors, for example sensors to measure, for example, deep body temperature, skin temperature, respiration rate, and combinations thereof. Disclosed embodiments can measure the presence of biomarkers in human exhaled breath.

Disclosed herein are temperature sensors, for example body temperature sensors, and methods of use thereof. For example, disclosed sensors can be used to measure the body temperature of, for example, a mammal such as a human. In embodiments the body temperature can comprise surface temperature or deeper body temperature.

In embodiments, a disclosed sensor comprises electrodes, for example silver interdigital electrodes (IDE). The electrodes can comprise a coating, for example a coating comprising carbon black thin sensing film. Further embodiments comprise a substrate. For example, disclosed embodiments can comprise a thermoplastic, for example a film substrate, for example a polyimide film such as KAPTON®. Embodiments comprise a 50 μm KAPTON® substrate chosen based on processing requirements and compatibility with the printable solutions i.e. silver and carbon black. Distinguishing properties of KAPTON® substrates are light weight, high temperature sustainability and conformability, making it suitable choices for wearable electronic and sensing applications.

In embodiments the substrate can comprise an appropriate thickness. For example, in embodiments, the thickness of the substrate can be, for example, 30 μm, 40 μm, 50 μm, 60 μm, 70 μm, or the like.

In embodiments, the substrate can comprise "fingers" or extensions as seen in FIG. 1. In embodiments, the spacing between fingers can be, for example, between 0.1 mm and 1 mm. In embodiments, sensitivity of 0.00375° C.-1 was achieved.

In embodiments, disclosed sensors are low cost and biocompatible. In embodiments, a disclosed sensor comprises, for example, a polyimide (PI) substrate, silver nanoparticles IDE, carbon black sensing film, PDMS encapsulation, and silver connecting pads.

In embodiments, a disclosed sensor can produce linear and stable temperature readings at a range of, for example, 28 to 50° C. Disclosed embodiments can comprise a response and recovery time of, for example, 4 sec and 8.5 sec respectively for, for example, 30, 40, or 50 or more days.

In embodiments, disclosed sensors are flexible. For example, in disclosed embodiments a disclosed sensor can exhibit bendability down to 5 mm diameter and was also tested on human body for temperature reading on the wrist and finger. In embodiments, disclosed sensors can resist change due to temperature, surface morphology and chemical characteristics of the sensing film through Raman shift.

Disclosed sensors can be used by, for example, placing them on the skin. In embodiments, the sensor can be shaped to fit a specific area of the body. For example, for use on the face, and embodiment can be shaped in the form of a mask.

Disclosed embodiments comprise a human body temperature sensor deployed on the human wrist. In embodiments, the sensor is produced using a low-cost screen printing technology on a biocompatible substrate and with detection range between 28 to 50° C. In embodiments, the sensor can be used for three different applications; human body skin temperature, deep body temperature, and respiration rate sensing. In embodiments, the sensor is a resistive type; it provides variation in the terminal resistance against input entity. In embodiments, the sensor can easily interface with electronic processing circuits by using a simple voltage divider network, which converts the resistance variation into voltage variation for the further process.

The instant disclosure provides a block diagram depiction of a disclosed sensor device connected to the readout module. In embodiments, the sensor comprises a PI substrate, silver IDE, carbon black sensing film, and encapsulated with polydimethylsiloxane (PDMS) to avoid environmental effects.

The instant disclosure provides detail about the sensors' response and recovery time on a time scale. For example, for a response time recorded as 4 sec, it is the time of resistance transition from low to high (on the time scale from 2.2 to 6.2 sec). After the 4 sec duration, resistance of the sensor becomes stable. In embodiments, to analyze the recovery time, the sensor is removed from the skin and time is recorded for the resistance transition from high to low. The recovery time was recorded as 8.5 sec approximately.

The instant disclosure provides detail regarding a temperature sensing test on the human wrist. For this analysis, the sensor was connected to the source meter through leads and was placed on the wrist with the help of plastic tape. It can be seen in the figures that initially the sensor is attached on the wrist and shows high resistance on the Y-axis. As the sensor is detached from the wrist its resistance decreases gradually. After the recovery time sensor is again attached on the wrist and resistance is increased.

In one or more embodiments, the disclosure provides a human body temperature measurement sensor.

Figure 11:
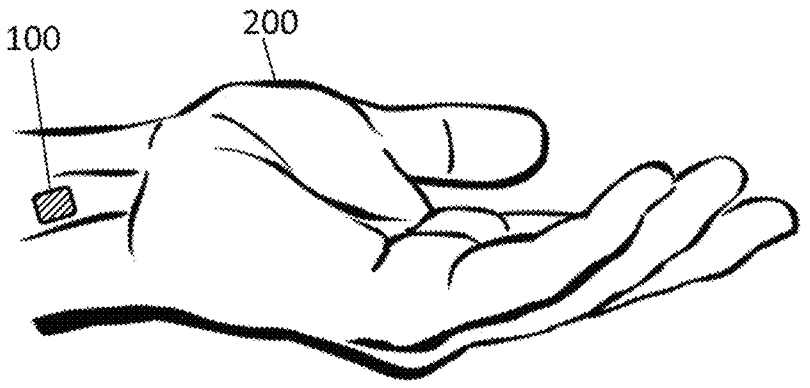
FIG. 11 shows a block diagram of a disclosed human body temperature sensor placed on a human wrist.
Figure 12:
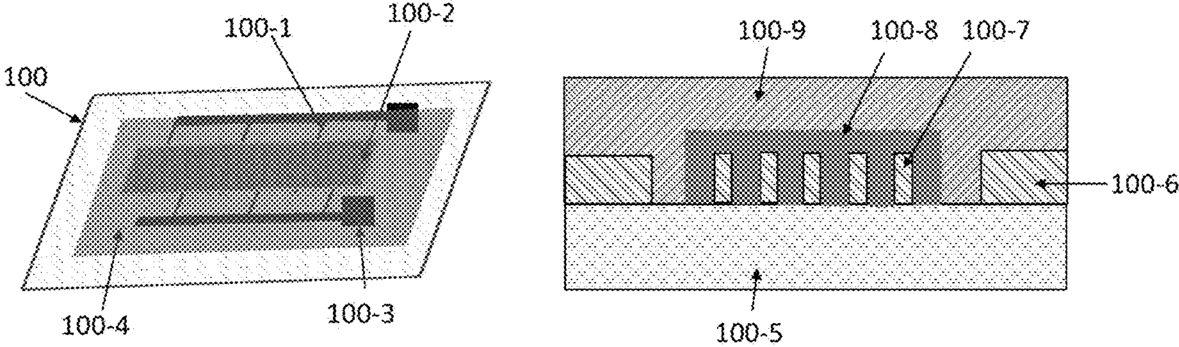
FIG. 12 shows a schematic diagram of a disclosed temperature sensor and its cross sectional view image in an embodiment.

FIG. 11 illustrates a block diagram of the human body temperature sensor placed on a human wrist 200, sensor device 100. FIG. 12 illustrates a schematic diagram of the temperature sensor. The sensor device comprises substrate 100, silver interdigital electrodes 100-1, sensing film 100-2, connecting pads 100-3, and encapsulation layer 100-4. The temperature sensor measures the human body surface temperature when it is mechanically attached with the body.

Figure 13:
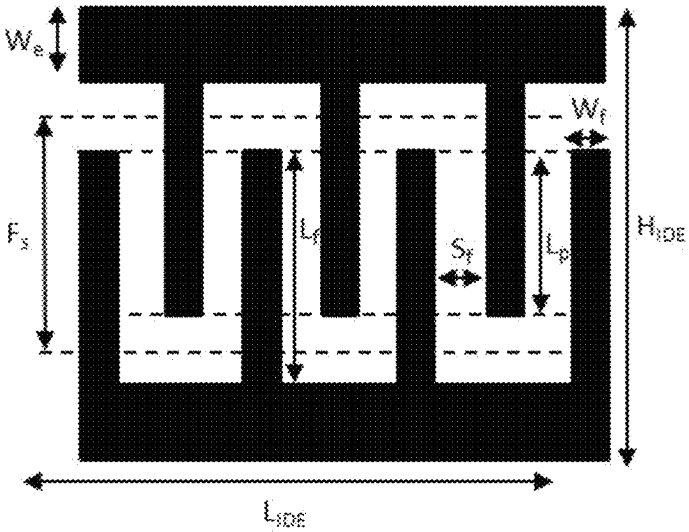
FIG. 13 shows a layout diagram of a disclosed human body temperature sensor with parameter sizes.
Figure 14:
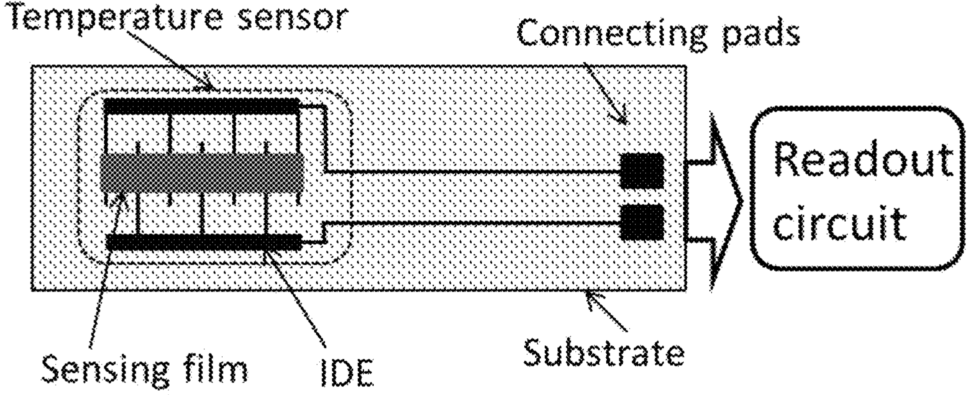
FIG. 14 shows a schematic diagram of a disclosed temperature sensor components and readout pads.
Figure 15:
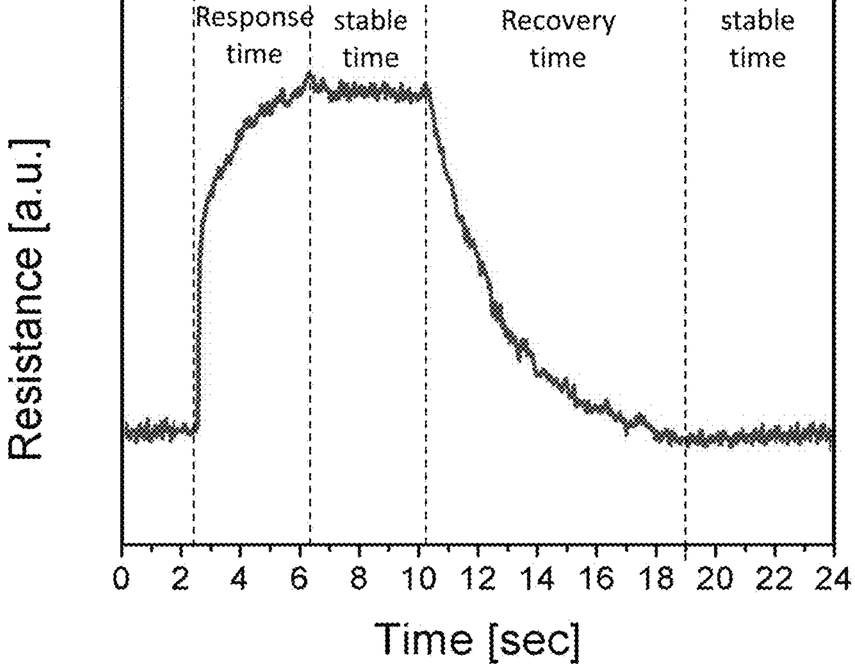
FIG. 15 shows experimental results of a disclosed temperature sensor, response and recovery time on the human body.
Figure 16:
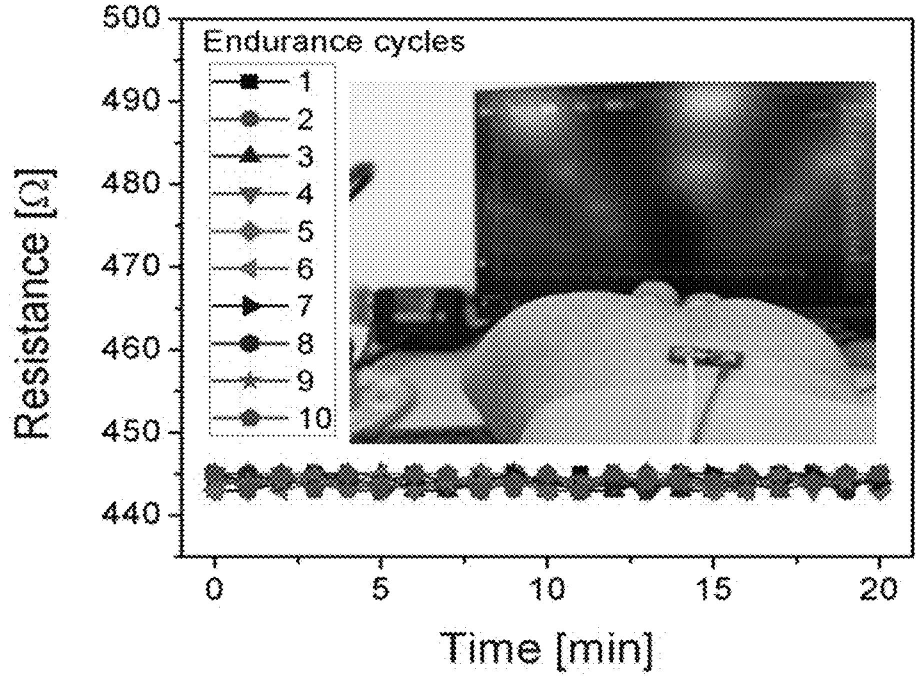
FIG. 16 shows experimental results of a disclosed temperature sensor, tested on a human wrist.

Resistance of the temperature sensor varies along with the body temperature; the resistance variation is correlated with temperature in Celsius. A cross-sectional view of the sensor is shown as substrate 100-5, connecting pads 100-6, interdigital electrodes 100-7, sensing film, and encapsulation layer 100-9. FIG. 13 illustrates the temperature sensor electrode parameters with sizes. The sensor's electrode parameters were experimentally tuned for linear response and high sensitivity to be as finger length ($L_f$=300 μm), finger spacing ($S_f$=300 μm), fingers parallel length ($L_p$=1.5 mm), finger width ($W_f$=300 μm), sensing film ($F_s$=1.8 mm), electrode width ($W_e$=1 mm), height of IDE ($H_{IDE}$=4 mm), and length of IDE ($L_{IDE}$=4 mm). FIG. 14 Illustrates a layout diagram of the human body temperature sensor consisted of substrate, IDE electrodes, sensing film, connecting wires and pads.

It is apparent that various modifications and variations can be made to the disclosed embodiments. It is intended that the specifications be considered as exemplary only.

Methods of Producing Body Temperature Sensors

Disclosed embodiments can comprise sensors made using, for example, a printer, such as an inkjet printer, for example a DMP-2850 or its equivalent. Disclosed embodiments can comprise use of a "doctor blade" to remove ink from a substrate.

In embodiments, interdigital electrodes (IDEs) are printed using, for example, a silver (Ag) nanoparticle solution. In embodiments, Ag nanoparticles loading of ~40% in ethylene glycol at the viscosity i.e. ~10 cP can be required for the material inkjet systems. In embodiments, the sensing layer comprises carbon black, which can be mixed in ethylene glycol at ~18 wt. %. The synthesized solution had a viscosity of ~22 cP, which is in suitable range for screen printing.

In embodiments, a disclosed temperature sensor is made by screen printing nanomaterial-based metal interdigital electrodes (IDEs) and filled with the temperature sensing layer. An equal spacing between the electrodes is maintained to ensure containment of the sensing layer and exposure to the detection event without being interrupted by the surrounding environment. In embodiments, the interconnection and pads are also printed by using the same metallic ink for the readout. In embodiments, a thin encapsulant layer is applied on the sensing layer as well as on the metal electrodes. The encapsulant layer plays an important role in the device performance as the metal electrodes are prone to oxidation and the temperature sensing layer is sensitive to humidity. In embodiments, the encapsulant layer can be applied on the entire device using a screen printing technology.

METHODS OF USE

In embodiments, disclosed sensors can be used by contacting them to human skin, such as in a patch or mask.

EXAMPLES

The following non-limiting Examples are provided for illustrative purposes only in order to facilitate a more complete understanding of representative embodiments. This example should not be construed to limit any of the embodiments described in the present specification.

Example 1

Sensor Production

Prior to printing the sensors, the substrate was properly cleaned following a standard preparation protocol. Plastic substrates usually require wet cleaning procedures and surface treatments that help in enhancing the print quality and adhesion between functional material and target substrate. KAPTON® substrate was cleaned with acetone followed by isopropanol and deionized water respectively. Substrate was treated by UV activation in plasma etcher for 5 min.

A Dimatix DMP 2850 inkjet printing system was used for patterning the electrodes and doctor blade for the temperature sensing film. Usually, materials with viscosity of 10-12 cP are favorable for inkjet material printers to make micrometer sized droplets through the nozzle in combination with piezoelectric actuators. Volume of the droplets is partially dependent on the average particle size, viscosity, surface tension, and vaporization points of the solvents.

Process related control parameters that have a direct impact on the volume and speed of the droplet generation are the piezoelectric actuation controlled by pulsating waveforms, voltages, jetting frequencies, meniscus set-point, orifice size of the nozzle, and the stand-off distance of print head from the target substrate. IDEs were designed using commercially available ACE-3000 design tool. Dimensions of the sensing electrodes and inter-finger spacing were experimentally validated and the optimized designs were selected for the sensor fabrication.

The designed file was converted into computer compatible, e.g. .bmp and .ptn file format, for the DMP-2850 inkjet printer. Silver ink was filled in the reservoir (3 ml) and 10 μL of 16 nozzles piezoelectric cartridge. Substrate was placed on the platen and desired pattern of the interdigital electrode was loaded along with setting various parameters of the printer such as platen temperature 35° C., dripping frequency 1 kHz, standoff distance 100 μm and 16 number of nozzles. The printing parameters such as jetting waveform, drop velocity (7 mm/sec), and droplet spacing at 25 μm were selected in the Dimatix drop manager window. All these parameters were adjusted based on the experimental outcomes by using the Ag ink several trials.

Two printing cycles were executed to increase the layer thickness that enhances the electrical conductivity as well as the mechanical robustness and adhesion of the Ag patterns to the KAPTON® substrate. The printed structure was sintered at 200° C., for 1 hour as recommended by the ink supplier. The sample was then loaded in the doctor blade machine for the deposition of carbon black film on the IDE. Carbon ink was deposited with the help of mask pattern that covers the overlapped area of electrode fingers. The fabrication process of the IDE and carbon film is shown in FIG. 1(*a*). The device was cured at 150° C. in a furnace after the deposition of carbon film. Copper wires were connected to the electrodes in order to make it accessible for the electrical characterization. Fabricated devices are shown in FIG. 1(*b*) both encapsulated and without encapsulation. Encapsulation plays an important role in the device performance as Ag is prone to oxidation and carbon film is sensitive to humidity and gasses. After the encapsulation, the device was stable at electrical resistance vs temperature. Two-part silver based conductive epoxy (EPO-TEK) was mixed properly and applied at the connecting pads while contacting the connecting wires.

A hotplate at 100° C. was used to partially cure the conductive epoxy while applying at the pads. A final heat treatment at 150° C. was used to complete the silver conductive epoxy curing, establishing a mechanically strong and electrically conductive connection.

Quality of the printed films depends both on the physical and electrical characteristics of the films and patterns. In order to maintain a good quality of printing, fabrication processing parameters and substrate pretreatments need to be properly carried out, for example substrate cleaning and optimizing pattern width and thickness.

Figure 2:
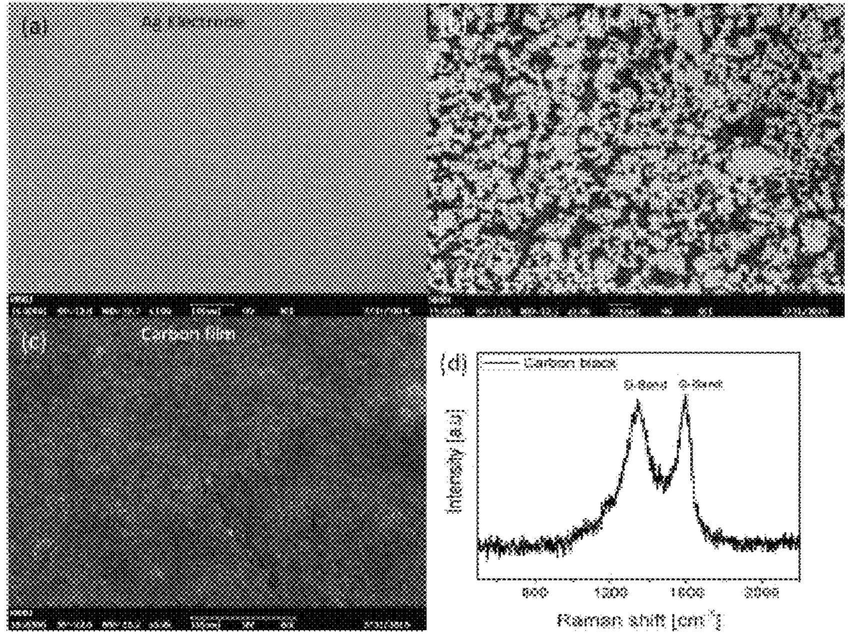
FIG. 2 shows an exemplary (a) Ag electrode, (b) Ag paste for the interconnection wires, (c) carbon thin film, and (d) Raman shift analysis of the carbon film.

IDE finger width (200 μm) and gap between fingers (600 μm) with high accuracy were printed repeatedly without any noticeable variations. By using DMP 2850, an accuracy of ±5 μm was achieved by repeatedly printing the similar structures on KAPTON® substrates several times and the printed patterns remained in close proximity. In order to maintain a good conductivity (especially for the Ag electrodes), two printing passes were performed. Electrodes and sensing film have been investigated by SEM. FIG. 2(*a*) shows the micrographs of the Ag electrode at scale of 10 μm confirming the proper deposition and sintering. Ag nanoparticles are properly bonded with each other resulting into enhanced electrical conductivity. FIG. 2(*b*) shows micrograph of the Ag paste, which is used to establish connection for the measurement and readout purpose. FIG. 2(*c*) shows the SEM image of the carbon black film deposited on the Ag electrode.

The micrograph confirms the proper deposition and sintering of the carbon black film. Raman spectrum of the carbon black is shown in FIG. 2(*d*). It is composed of two peaks, D-band and G-band; the first band range is from 1260 to 1320 $cm^{-1}$, the G-band peak ranging from 1560 to 1610 $cm^{-1}$. The D line appears from sp2 hybridized carbon structure. The physical properties of the carbon black film are strongly correlated with the ratio of D and G bands types of C—C bonding. Mainly ratio of the sp3/sp2 carbon phases depends on fabrication conditions where it can be changed in a range from pure diamond to pure graphite. G-band peak represents the nearby atoms which are moving in opposite directions but perpendicular to the plane of the carbon black sheet. D-band peak represents the atoms moving in radial directions in the plane of the carbon black sheet.

Figure 3:
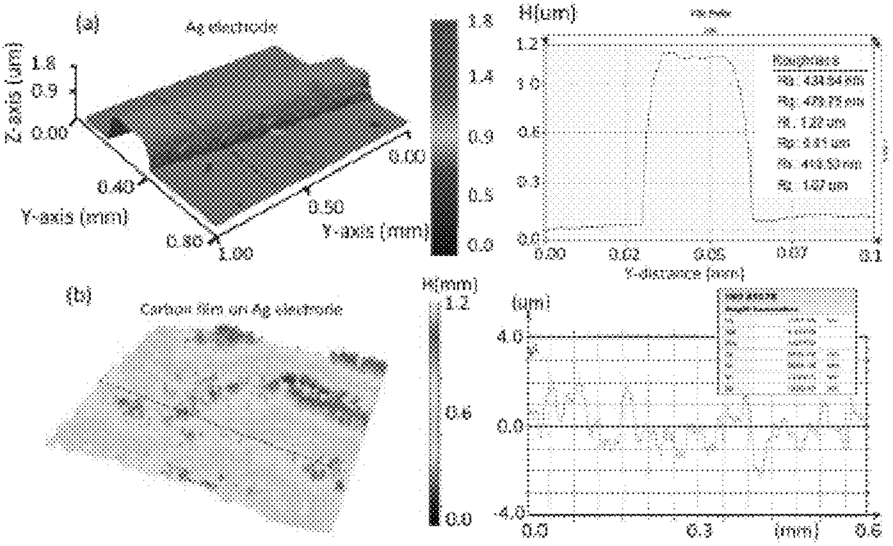
FIG. 3 shows an exemplary 3D Nano profile analysis (a) Ag electrode on KAPTON® substrate, and (b) carbon film deposited on an Ag electrode.

FIG. 3(*a*) shows 3D Nano profiler analysis of the Ag electrode printed on a KAPTON® substrate and the roughness analysis of the electrode. Printing cycles were kept at two in the experiment of Ag patterns in order to achieve the desired resistivity value at around 20 μΩ-cm after sintering in the oven at 200° C. Multiple numbers of printing passes were used for the conductivity of pattern if the finger spacing is wide enough to accommodate spreading of the ink on the substrate.

In our case the spacing between the fingers is 600 μm. From the 3D image, the height of the electrode finger is almost 1 μm and thickness of 200 μm. The electrodes are formed properly with good aspect ratio to assure the desired conductivity. Roughness chart is given in the inset of Y-direction plot of FIG. 3(*a*). Carbon film was deposited on the Ag electrodes through use of a doctor blade as shown in FIG. 3(*b*) (roughness table is shown in the inset where sq. value is 1707 nm).

Figure 4:
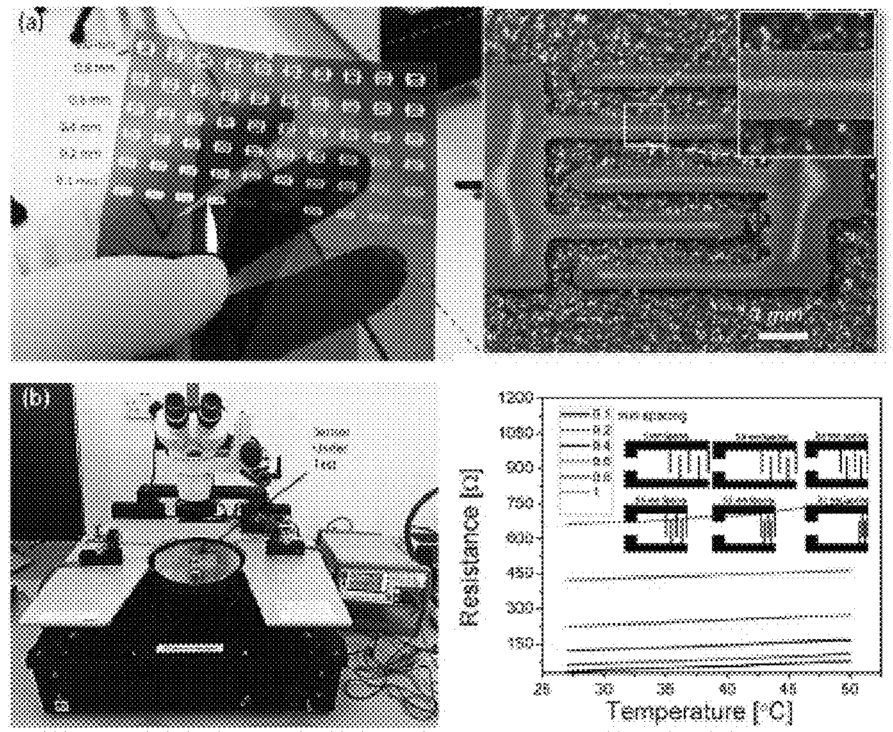
FIG. 4 shows an exemplary of (a) 6 types of electrodes with different finger spacing 1.0 mm to 0.1 mm, (b) electrical characterization of individual sensor for resistance variation against temperature change from 28 to 50° C.

Temperature sensors were optimized by varying the finger spacing of the electrodes. Six different electrodes with finger spacing 1.0 mm down to 0.1 mm were fabricated on PI substrate as shown in FIG. 4(*a*), the trace width was kept to 200 μm to make sure of Ag conductivity. Inset of FIG. 4(*a*) shows microscopic image of the electrode, it can be seen that the fingers of the electrode are properly deposited with uniform trace width throughout and there is no short circuit path between them. Carbon ink was deposited on the electrodes 1 mm wide and 1-2 μm thick on all the electrodes. Electrical characterization was done with source meter in combination with a probe station as shown in FIG. 4(*b*). It was observed that all the sensors gave a resistance change against the temperature variation from 20 to 50° C. but the base resistance was different for each type of sensor, and it was expected because space between the fingers is directly proportional to the resistance of the carbon film.

Resistance temperature detector (RTD) is a contact-based temperature sensor that changes its resistance along with the change in temperature. This variation in resistance caused by temperature change is used to detect the temperature of measuring body. The advantages of RTD type temperature sensors are small size, high accuracy, short response time and simple architecture. The TCR (temperature coefficient of resistance) can be calculated by the following equation:

$$TCR = \frac{R_b - R_a}{R_a(\Delta T)}$$

Here, $\Delta T = T_b - T_a$ is change in temperature of the sensor, $T_a$ is initial temperature at 28° C. of the sensor, $T_b$ is present temperature of the sensor, $R_a$ is initial resistance of the sensor at 28° C. and $R_b$ is current resistance at a particular temperature. The sensitivity of the temperature sensor is calculated by:

$$S_{sens} = \frac{\Delta R}{R_a}$$

Here, $S_{sens}$ is sensitivity, $\Delta R = R_b - R_a$. The variation in resistance with respect to temperature change was observed by using our proposed sensor for different sizes of patterns.

Figure 5:
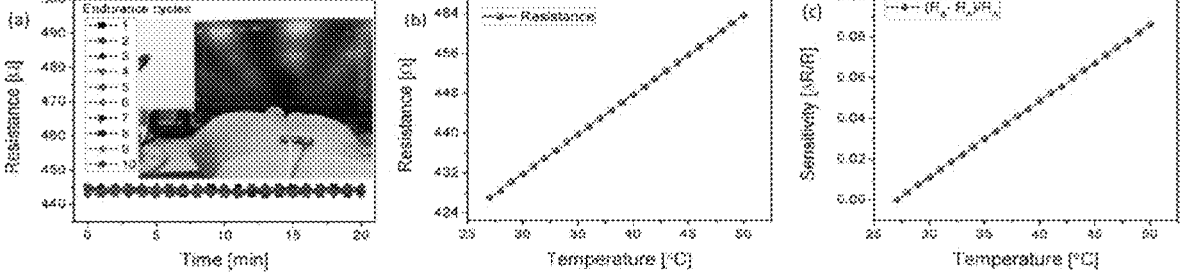
FIG. 5 shows an exemplary (a) sensor endurance test on human wrist, (b) resistance reading of the temperature sensor ranging 28 to 50° C., and (c) sensitivity analysis of the sensor.
Figure 6:
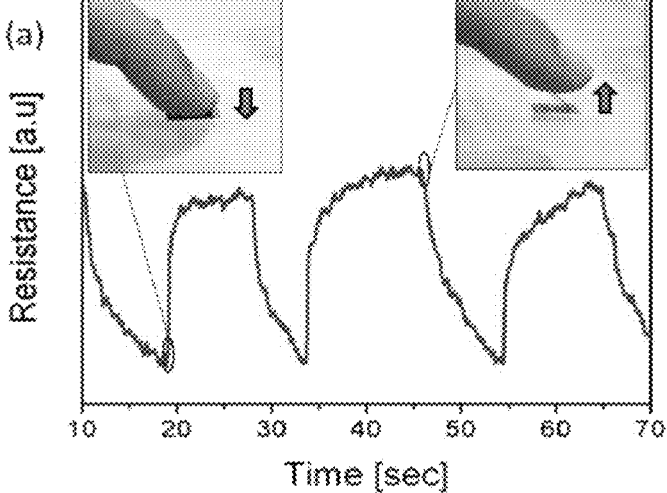
FIG. 6 shows an exemplary (a) temperature sensing by finger placing on the sensor, (b) attaching and detaching the sensor on the wrist.
Figure 6:
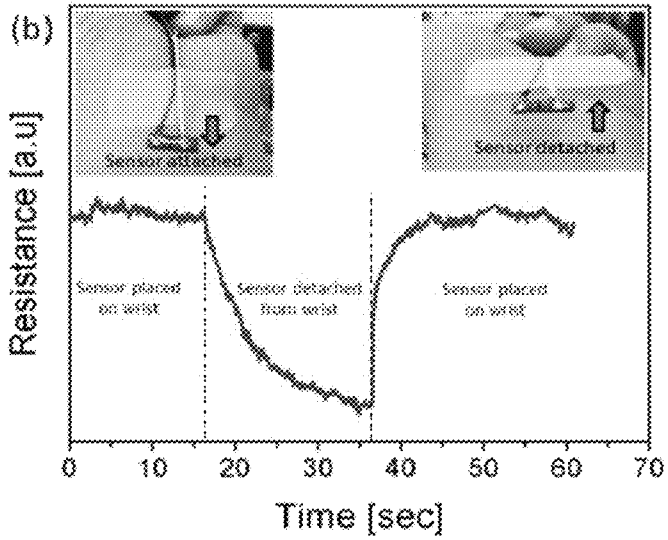

The sensor was analyzed for several temperature characteristics in order to measure the real time temperature of the human body. For this test, a temperature sensor was taped on the wrist and leads were connected to source meter for the resistance measurement as shown in the inset of FIG. 5(*a*). At human wrist temperature the sensor measured 445Ω. The sensor was tested for 10 endurance cycles each for 20 min to observe the stability of the sensor against human body temperature. The resistance deviation was recorded as ±1Ω (443-445Ω) during the test as shown in FIG. 6(*a*). The sensor showed a stable response. The sensor was tested for the temperature span of 28 to 50° C. to analyze the stability of the device against temperature variations. The sensor was placed on a variable temperature plate and leads of the sensor were connected to the source meter. Temperature of the sensor holding plate was increased by 1° C. and resistance was recorded as shown FIG. 5(*b*). It was observed that the sensor's behavior is linear throughout the temperature range and repeatable. Although the targeted application of the proposed sensor is human body temperature measurement, the temperature range of from 28 to 50° C. increase the suitability of the sensor for uses such as on robotic artificial skin. Sensitivity of the sensor was calculated from the measured data of the resistance against temperature by using Equation 2. FIG. 5(*c*) shows sensitivity data of the sensor for the temperature range of 28 to 50° C.

In order to characterize the sensor on human body, FIG. 6(*a*) shows temperature sensing test of the sensor by placing a finger on the sensor. The sensor was encapsulated with silicone epoxy to avoid electrical contact between finger and sensor. The sensor was placed in such a position so that encapsulated side was facing down and finger was brought into contact from the substrate side covering the effective area of the sensor. Results show, when finger is placed on the sensor, due to the finger's temperature the resistance of the sensor increases and when the finger is not in the contact the resistance recovers to the initial values. Although a human finger is not suitable for the temperature reading, nonetheless the change in resistance is prominent because of the high sensitivity of the sensor.

FIG. 6(*b*) shows a temperature sensing test on the human wrist. For this analysis, sensor was connected to the source meter through leads and was placed on the wrist with the help of plastic tape. It can be seen in the figure; initially the sensor is attached on the wrist shows high resistance on the Y-axis. As the sensor is detached from the wrist its resistance decreases gradually. After the recovery time sensor is again attached on the wrist and resistance is increased. This resistance change is between the human body and room temperature, at the testing time room temperature was 24° C.

Figure 7:
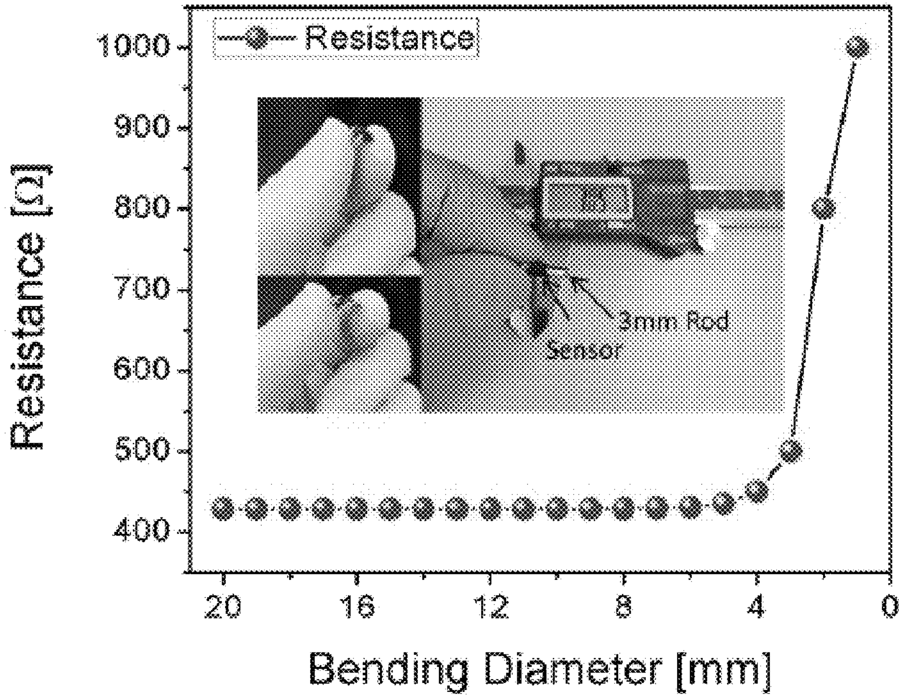
FIG. 7 shows an exemplary bending analysis of a disclosed sensor.

The sensor was characterized for its bendability characteristics to find the maximum bending limit as the sensor is supposed to be utilized in the wearable electronics. For this characterization sensor was bent over the metallic rods of various diameters (20 mm down to 1 mm). From 20 mm to 5 mm the sensor did not show any change in the electrical resistance at 28° C. temperature as shown in FIG. 7. The inset shows the sensor bending on a metallic rod measured with digital vernier caliper. Below the 5 mm bending diameter, the sensor resistance increased to 1000Ω from initial resistance of 424Ω, effectively due to the carbon film cracks. Thus, the sensor can be used within the limits of bending 5 mm diameter.

Figure 8:
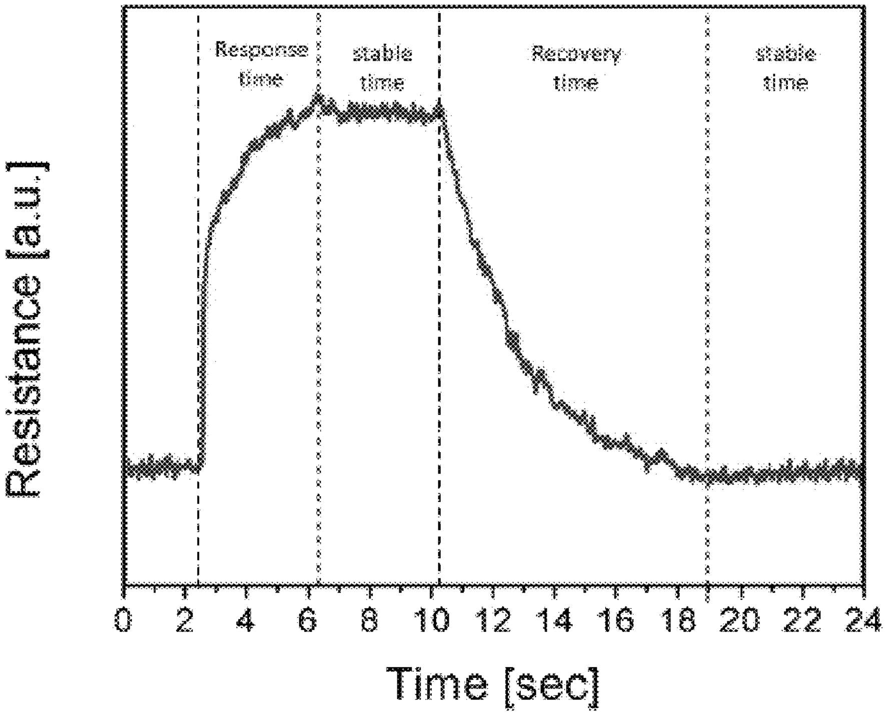
FIG. 8 shows an exemplary response and recovery time analysis of the sensor.

Response and recovery time analysis of the sensor was carried out. The sensor was connected to a source meter and placed on a human wrist in order to record the response time. Initially the sensors' resistance was low, then due to temperature the resistance reached a high value and became stable. A delay of 4 sec was recorded as response time of the sensor as shown in FIG. 8. Response time was recorded as 4 sec, it is the time of resistance transition from low to high (on the time scale from 2.2 to 6.2 sec). After the 4 sec interval, resistance of the sensor became stable.

To analyze the recovery time, the sensor was removed from the wrist and time was recorded for the resistance transition from high to low as shown in FIG. 8. The recovery time was recorded as 8.5 sec approximately. The resistance reading of the sensor over the time was recorded for 50 days as shown in FIG. 9. It was found that encapsulated sensor exhibited stable behavior over the span of 50 days where only 1.196Ω drift was recorded between day 1 and day 50. This characterization of the time span assures that the proposed sensor is robust enough to be used as wearable electronics for temperature reading.

FIG. 10 shows a comparison of the proposed sensor with those reported in few of the reported related researches. All sensors listed in the figure are temperature sensors with different temperature range, material, geometry and sensing type i.e. resistive or capacitive. Sensors can comprise graphene oxide in combination with IDE where the capacitance changes against a temperature change and the sensitivity is 80 pF/° C. This sensor shows good sensitivity and response/recovery time relatively, but it is based on capacitive detection which requires a readout circuit. In our proposed idea the sensor is resistive and does not require readout circuit but a resistor to form a voltage divider network and voltage against the sensor is read directly by the electronic system i.e. microcontroller or PC. Rest of the sensors provided in the figure are resistive, but their performance is not better than the proposed sensor in terms of sensitivity and response recovery time.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present disclosure, which is defined solely by the claims. Accordingly, embodiments of the present disclosure are not limited to those precisely as shown and described.

Certain embodiments are described herein, comprising the best mode known to the inventor for carrying out the methods and devices described herein. Of course, variations on these described embodiments will become apparent to those of ordinary skill in the art upon reading the foregoing description. Accordingly, this disclosure comprises all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

Groupings of alternative embodiments, elements, or steps of the present disclosure are not to be construed as limitations. Each group member may be referred to and claimed individually or in any combination with other group members disclosed herein. It is anticipated that one or more members of a group may be comprised in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the disclosure are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope otherwise claimed. No language in the present specification should be construed as indicating any non-claimed element essential to the practice of embodiments disclosed herein.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present disclosure so claimed are inherently or expressly described and enabled herein.

Disclosed embodiments can comprise:

Embodiment 1—A low-cost and scalable screen printed wearable sensor for real-time human body temperature measurement.

Embodiment 2—The sensor device according to Embodiment 1, further comprising:

a. Low-cost printed sensor directly on a PI substrate. The printed sensor is flexible, conformable and can become an integral part of a wearable system. The sensor can be shaped for applications such as wrist band, facial mask, fabric, or any non-planar substrate that interacts with human body for the temperature reading.

Embodiment 3—The sensor according to Embodiment 1, further comprising:

a. The temperature measurement is used for prolonged analysis of the human body skin and deep body temperature. The same sensor can be used for deep body temperature measurement when deployed on a facial mask that can be placed on the mouth or nose to interact with human breath.
b. The sensor is ideal for breath monitoring as the temperature variation is significant during the inhale and exhale cycle. This data is very important for patient dealing with various chronic diseases and continuous monitoring of the health condition gives a deeper insight into the health condition.

Embodiment 4—The sensor device according to Embodiment 1, further comprising:

a. The human body temperature sensor can be used as a respiration rate sensor when used in a mask placed on mouth or nose. During the inhale and exhale of breath, the temperature varies on the surface of sensor that leads to resistance variation. Variation in resistance provides information about the breathing rate (respiration rate) on the time scale. For a normal human the respiration rate is 12 to 20 breathes per second.

Embodiment 5—The sensor according to Embodiment 1, further comprising:

a. The human body temperature sensor has the characteristic to be worn easily as the printed materials are conformable to uneven surfaces and foldability or stretchability has less impact on the overall performance of the sensor.

Embodiment 6—The sensor according to Embodiment 1, further comprising:

a. The materials used are biocompatible and poses no threats or harm to the wearer's health. Also, the sensor is encapsulated with biocompatible material i.e. PDMS that provides protection to the sensor against varying environmental impacts.

Embodiment 7—The sensor according to Embodiment 1, further comprising:

a. The sensor design is simple and can easily be changed for target application, as the manufacturing through printing technology offers the possibility to make changes abruptly.

Embodiment 8—The sensor according to Embodiment 1, further comprising:

a. The sensor has the characteristics to be developed on a wide variety of substrates, so it provides a room for further applications.

Embodiment 9—The sensor according to Embodiment 1, further comprising:

a. The sensor can be scaled up for mass production through screen printing technology that drastically reduces the unit cost.

The invention claimed is:

1. A sensor comprising:

a first deposition of silver ink on a substrate with an inkjet material printer at room temperature, a second deposition of silver ink on the substrate with the inkjet material printer at room temperature, wherein the first deposition and second deposition comprise a silver based interdigital electrode, a carbon black film deposited on the silver based interdigital electrode, and at least two terminals, wherein a finger spacing of the interdigital electrode is between 0.1 mm and 0.3 mm, wherein said sensor comprises a temperature sensor, wherein said temperature sensor comprises a wearable temperature sensor for real-time measurement of skin surface temperature or deep body temperature, wherein the substrate comprises a substrate of said wearable temperature sensor, and wherein the substrate comprises a non-planar substrate, wherein said non-planar substrate comprises a facial mask.

2. The sensor of claim 1, wherein said measurement comprises measurement of skin surface temperature.

3. The sensor of claim 1, wherein said measurement comprises measurement of deep body temperature.

4. The sensor of claim 1, wherein said wearable temperature sensor is configured for measuring temperature variation during an inhale and exhale cycle.

5. The sensor of claim 4, wherein said measuring temperature variation during the inhale and exhale cycle comprises measurement of resistance changes of said wearable temperature sensor as a result of temperature changes.

* * * * *